United States Patent
Sekar et al.

(10) Patent No.: US 11,191,802 B2
(45) Date of Patent: Dec. 7, 2021

(54) COMPOSITION FOR CONTROLLED RELEASE OF THERAPEUTIC AGENTS

(71) Applicant: AMMA Therapeutics, Inc., Hayward, CA (US)

(72) Inventors: Michael M. Sekar, Palo Alto, CA (US); Manish Singhal, San Mateo, CA (US)

(73) Assignee: AMMA Therapeutics, Inc., Hayward, CA (US)

(*) Notice: Subject to any disclaimer, the term of this patent is extended or adjusted under 35 U.S.C. 154(b) by 0 days.

(21) Appl. No.: 16/376,930

(22) Filed: Apr. 5, 2019

(65) Prior Publication Data
US 2019/0307834 A1 Oct. 10, 2019

Related U.S. Application Data

(60) Provisional application No. 62/653,951, filed on Apr. 6, 2018.

(51) Int. Cl.
| | | |
|---|---|---|
| *A61K 38/10* | (2006.01) | |
| *A61K 38/08* | (2019.01) | |
| *C07K 14/715* | (2006.01) | |
| *A61K 38/17* | (2006.01) | |
| *A61K 31/451* | (2006.01) | |
| *A61K 31/135* | (2006.01) | |
| *A61K 38/28* | (2006.01) | |

(52) U.S. Cl.
CPC ............ *A61K 38/10* (2013.01); *A61K 31/135* (2013.01); *A61K 31/451* (2013.01); *A61K 38/08* (2013.01); *A61K 38/1709* (2013.01); *A61K 38/28* (2013.01); *C07K 14/7151* (2013.01); *C07K 2319/30* (2013.01)

(58) Field of Classification Search
CPC ........ A61K 38/10; A61K 38/08; A61K 38/04; A61K 38/16; C07K 7/00; C07K 7/06; C07K 7/08; C07K 9/00; C07K 14/00
See application file for complete search history.

(56) References Cited

U.S. PATENT DOCUMENTS

| | | | |
|---|---|---|---|
| 4,675,381 A | 6/1987 | Bichon | |
| 2011/0311594 A1 | 12/2011 | Chen et al. | |

FOREIGN PATENT DOCUMENTS

| | | |
|---|---|---|
| WO | WO-2001/047549 | 7/2001 |
| WO | WO-2004/043432 | 5/2004 |
| WO | WO-2012/131106 | 10/2012 |

OTHER PUBLICATIONS

International Search Report and Written Opinion for PCT/US2019/026120 dated Sep. 12, 2019, 12 pages.
Panda et al., "Self-assembled nanoparticles based on modified cationic dipeptides and DNA: novel systems for gene delivery", Journal of Nanobiotechnology, Jun. 21, 2013, vol. 11, pp. 1-13.

*Primary Examiner* — Lianko G Garyu
(74) *Attorney, Agent, or Firm* — Sheppard Mullin Richter & Hampton LLP

(57) ABSTRACT

Provided are novel peptides, methods of their preparation and their use in controlled release of pharmaceutically active compounds.

17 Claims, 10 Drawing Sheets
Specification includes a Sequence Listing.

SEQUENCE LISTING

<160> NUMBER OF SEQ ID NOS: 16

<210> SEQ ID NO 1
<211> LENGTH: 15
<212> TYPE: PRT
<213> ORGANISM: Artificial Sequence
<220> FEATURE:
<223> OTHER INFORMATION: Synthetic

<400> SEQUENCE: 1

Arg Arg Arg Arg Arg Leu Leu Leu Leu Leu Glu Glu Glu Glu Glu
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic

<400> SEQUENCE: 2

Arg Arg Arg Arg Arg Arg Leu Leu Leu Ala Ala Ala Glu Glu Glu
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic

<400> SEQUENCE: 3

Lys Lys Lys Lys Lys Lys Leu Leu Leu Ala Ala Ala Glu Glu Glu
1               5                   10                  15

<210> SEQ ID NO 4
<211> LENGTH: 13
<212> TYPE: PRT
<213> ORGANISM: Artificial Sequence
<220> FEATURE:
<223> OTHER INFORMATION: Synthetic

<400> SEQUENCE: 4

Arg Arg Arg Arg Arg Leu Leu Leu Ala Ala Ala Glu Glu
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Arg Arg Arg Leu Leu Leu Glu Glu Glu
1               5

<210> SEQ ID NO 6
<211> LENGTH: 13
<212> TYPE: PRT
<213> ORGANISM: Artificial Sequence
<220> FEATURE:
<223> OTHER INFORMATION: Synthetic

<400> SEQUENCE: 6

Arg Arg Arg Arg Arg Leu Leu Leu Glu Glu Glu Glu Glu
1               5                   10

```
<210> SEQ ID NO 7
<211> LENGTH: 15
<212> TYPE: PRT
<213> ORGANISM: Artificial Sequence
<220> FEATURE:
<223> OTHER INFORMATION: Synthetic

<400> SEQUENCE: 7

Glu Glu Glu Glu Glu Leu Leu Leu Leu Leu Arg Arg Arg Arg Arg
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic

<400> SEQUENCE: 8

Arg Arg Arg Arg Arg Leu Leu Leu Leu Leu Asp Asp Asp Asp Asp
1               5                   10                  15

<210> SEQ ID NO 9
<211> LENGTH: 6
<212> TYPE: PRT
<213> ORGANISM: Artificial Sequence
<220> FEATURE:
<223> OTHER INFORMATION: Synthetic

<400> SEQUENCE: 9

Arg Arg Arg Glu Glu Glu
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic

<400> SEQUENCE: 10

Leu Leu Leu Glu Glu Glu
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic

<400> SEQUENCE: 11

Arg Arg Arg Leu Leu Leu
1               5

<210> SEQ ID NO 12
<211> LENGTH: 10
<212> TYPE: PRT
<213> ORGANISM: Artificial Sequence
<220> FEATURE:
<223> OTHER INFORMATION: Synthetic

<400> SEQUENCE: 12

Arg Arg Arg Arg Arg Glu Glu Glu Glu Glu
1               5                   10
```

```
<210> SEQ ID NO 13
<211> LENGTH: 10
<212> TYPE: PRT
<213> ORGANISM: Artificial Sequence
<220> FEATURE:
<223> OTHER INFORMATION: Synthetic

<400> SEQUENCE: 13

Leu Leu Leu Leu Leu Arg Arg Arg Arg Arg
1               5                   10

<210> SEQ ID NO 14
<211> LENGTH: 15
<212> TYPE: PRT
<213> ORGANISM: Artificial Sequence
<220> FEATURE:
<223> OTHER INFORMATION: Synthetic

<400> SEQUENCE: 14

Arg Arg Arg Leu Leu Leu Glu Glu Glu Leu Leu Leu Arg Arg Arg
1               5                   10                  15

<210> SEQ ID NO 15
<211> LENGTH: 14
<212> TYPE: PRT
<213> ORGANISM: Artificial Sequence
<220> FEATURE:
<223> OTHER INFORMATION: Synthetic

<400> SEQUENCE: 15

Arg Arg Arg Arg Arg Arg Arg Glu Glu Glu Glu Glu Glu Glu
1               5                   10

<210> SEQ ID NO 16
<211> LENGTH: 21
<212> TYPE: PRT
<213> ORGANISM: Artificial Sequence
<220> FEATURE:
<223> OTHER INFORMATION: Synthetic

<400> SEQUENCE: 16

Arg Arg Arg Arg Arg Arg Arg Leu Leu Leu Leu Leu Leu Leu Glu Glu
1               5                   10                  15

Glu Glu Glu Glu Glu
            20
```

COMPOSITION FOR CONTROLLED RELEASE OF THERAPEUTIC AGENTS

CROSS-REFERENCE TO RELATED APPLICATIONS

This application claims the benefit under 35 U.S.C. § 119(e) to U.S. Provisional Application Ser. No. 62/653,951, filed on Apr. 6, 2018, the entirety of which is incorporated herein by reference.

SEQUENCE LISTING

The instant application contains a Sequence Listing which has been submitted in ASCII format via EFS-Web and is hereby incorporated by reference in its entirety. Said ASCII copy, created on May 16, 2019, is named 60HH-271320-US_ST25.txt and is 4,096 bytes in size.

FIELD

The present disclosure relates generally to novel peptides and their use in controlled release of pharmaceutically active compounds.

BACKGROUND

Parenteral controlled release systems offer an advantage of reduction in number of dosing or injections. Depots and implants are used which can work for months to year. These delivery systems deliver drug locally or to systemic circulation at a controlled rate. Parenteral dosages forms with prolonged actions are of medical and economic importance. The delivery of drugs, including injectable drug formulations, is often accomplished by the use of drug delivery matrix using mechanisms such as micro-encapsulation, phase-inversion and diffusion. Following injection, drug delivery matrix generally release drug in a slow and controlled manner. Drug delivery matrix can also reduce and/or eliminate the need for multiple injections. Such matrix often include at least diffusion controlling inactive excipients such as polymer, solvent, and drug. In some cases, the drug is highly soluble in the matrix and may leave the matrix too quickly. In other cases, the drug is unstable in the matrix.

According to Higuchi model, transport of a drug within the matrix or depot is crucial for drug release kinetics and is related to the diffusivity and the solubility of drug dissolved in a homogeneous medium.

The traditional depot approach though considered the solubility of pharmaceutically active drug in the matrix but did not take the solubility of the drug in an aqueous medium where it got injected (e.g. containing both solid and liquid phases).

The present disclosure addresses these and related issues and provides improved compositions for the controlled release of pharmaceutically active agents along with methods of making and using the same.

SUMMARY

Natural amino acids of different kind can be of different molecular characteristics including constituting polar, non-polar and hydrophobic or lipophilic functional groups due to dipole moment of each atom in every functional group. The present disclosure generally provides compositions comprising novel peptides, method of making them and method of using them for a controlled release of a pharmaceutically active agent. The peptide, comprising a unique combination of acidic, neutral and basic amino acids, is non-covalently bonded with or used in combination with the pharmaceutically active compound so as to allow for the controlled release of the pharmaceutically active compound.

In one embodiment, this disclosure provides a composition comprising:
i) a pharmaceutically active compound having a log P value of less than 4; and
ii) a peptide of formula I':

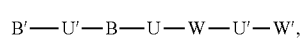

$$B'\text{—}U'\text{—}B\text{—}U\text{—}W\text{—}U'\text{—}W', \quad I'$$

wherein:
each of B, B', W and W' independently is a peptide comprising at least 75% acidic amino acids or 75% basic amino acids, provided that when B is a peptide having at least 75% acidic amino acids, W is a peptide having at least 75% basic amino acids or vice versa;
each of U and U' independently is a peptide comprising neutral amino acids;
each of B, U and W independently comprises 2 to 9 amino acids; and
each of B', U' and W' independently comprises 2 to 9 amino acids or the adjacent U' and W' are absent or the adjacent B' and U' are absent or all B', U' and W' are absent; provided that the peptide of formula I' comprises from about 9 to 21 amino acids.

In another embodiment, this disclosure provides a composition comprising:
i) a pharmaceutically active compound having a log P value of less than 4; and
ii) a peptide of formula I:

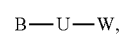

$$B\text{—}U\text{—}W, \quad I$$

wherein:
each of B and W independently is a peptide comprising at least 75% acidic amino acids or 75% basic amino acids, provided that when B is a peptide having at least 75% acidic amino acids, W is a peptide having at least 75% basic amino acids or vice versa;
U is a peptide comprising neutral amino acids; and
each of B, U and W independently comprises 2 to 9 amino acids, provided that the peptide of formula I comprises from about 9 to 21 amino acids.

In another embodiment, this disclosure provides a composition comprising:
i) a pharmaceutically active compound having a log P value of less than 4; and
ii) a peptide of formula RRRRRLLLLLEEEEE (SEQ ID NO:1).

In another embodiment, this disclosure provides a controlled release formulation comprising:
i) a pharmaceutically active compound having a log P value of less than 4; and
ii) a peptide of formula I':

$$B'\text{—}U'\text{—}B\text{—}U\text{—}W\text{—}U'\text{—}W', \quad I'$$

wherein:
each of B, B', W and W' independently is a peptide comprising at least 75% acidic amino acids or 75% basic amino acids, provided that when B is a peptide having at least 75% acidic amino acids, W is a peptide having at least 75% basic amino acids or vice versa;
each of B', U' and W' independently comprises 2 to 9 amino acids or the adjacent U' and W' are absent or the adjacent B' and U' are absent or all B', U' and W' are absent; provided that the peptide of formula I' comprises from about 9 to 21 amino acids,
wherein release of the pharmaceutically active compound is controlled by adjusting weight ratio of the pharmaceutically active compound to the peptide of formula I'.

In another embodiment, this disclosure provides a controlled release formulation comprising:
i) a pharmaceutically active compound having a log P value of less than 4; and
ii) a peptide of formula I:

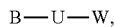

wherein:
each of B and W independently is a peptide comprising at least 75% acidic amino acids or 75% basic amino acids, provided that when B is a peptide having at least 75% acidic amino acids, W is a peptide having at least 75% basic amino acids or vice versa;
U is a peptide comprising neutral amino acids; and
each of B, U and W independently comprises 2 to 9 amino acids, provided that the peptide of formula I comprises from about 9 to 21 amino acids,
wherein release of the pharmaceutically active compound is controlled by adjusting weight ratio of the pharmaceutically active compound to the peptide of formula I.

In another embodiment, this disclosure provides a peptide of formula I':

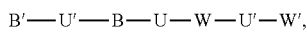

wherein:
each of B, B', W and W' independently is a peptide comprising at least 75% acidic amino acids or 75% basic amino acids, provided that when B is a peptide having at least 75% acidic amino acids, W is a peptide having at least 75% basic amino acids or vice versa;
each of B', U' and W' independently comprises 2 to 9 amino acids or the adjacent U' and W' are absent or the adjacent B' and U' are absent or all B', U' and W' are absent; provided that the peptide of formula I' comprises from about 9 to 21 amino acids.

In another embodiment, this disclosure provides a peptide of formula I:

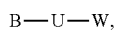

wherein:
each of B and W independently is a peptide comprising at least 75% acidic amino acids or 75% basic amino acids, provided that when B is a peptide having at least 75% acidic amino acids, W is a peptide having at least 75% basic amino acids or vice versa;
U is a peptide comprising neutral amino acids; and
each of B, U and W independently comprises 2 to 9 amino acids, provided that the peptide of formula I comprises from about 9 to 21 amino acids.

In another embodiment, this disclosure provides a drug delivery method comprising administering to a subject in need thereof a composition comprising:
i) a pharmaceutically active compound having a log P value of less than 4; and
ii) a peptide of formula I':

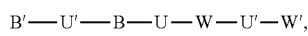

wherein:
each of B, B', W and W' independently is a peptide comprising at least 75% acidic amino acids or 75% basic amino acids, provided that when B is a peptide having at least 75% acidic amino acids, W is a peptide having at least 75% basic amino acids or vice versa;
each of U and U' independently is a peptide comprising neutral amino acids;
each of B, U and W independently comprises 2 to 9 amino acids; and
each of B', U' and W' independently comprises 2 to 9 amino acids or the adjacent U' and W' are absent or the adjacent B' and U' are absent or all B', U' and W' are absent; provided that the peptide of formula I' comprises from about 9 to 21 amino acids.

In another embodiment, this disclosure provides a drug delivery method comprising administering to a subject in need thereof a composition comprising:
i) a pharmaceutically active compound having a log P value of less than 4; and
ii) a peptide of formula I:

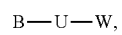

wherein:
each of B and W independently is a peptide comprising at least 75% acidic amino acids or 75% basic amino acids, provided that when B is a peptide having at least 75% acidic amino acids, W is a peptide having at least 75% basic amino acids or vice versa;
U is a peptide comprising neutral amino acids; and
each of B, U and W independently comprises 2 to 9 amino acids, provided that the peptide of formula I comprises from about 9 to 21 amino acids.

Other features and advantages of the present disclosure will be set forth in the description of invention that follows, and in part will be apparent from the description or may be learned by practice of the invention. The invention will be realized and attained by the compositions and methods particularly pointed out in the written description and claims hereof.

DETAILED DESCRIPTION

Figure 1:
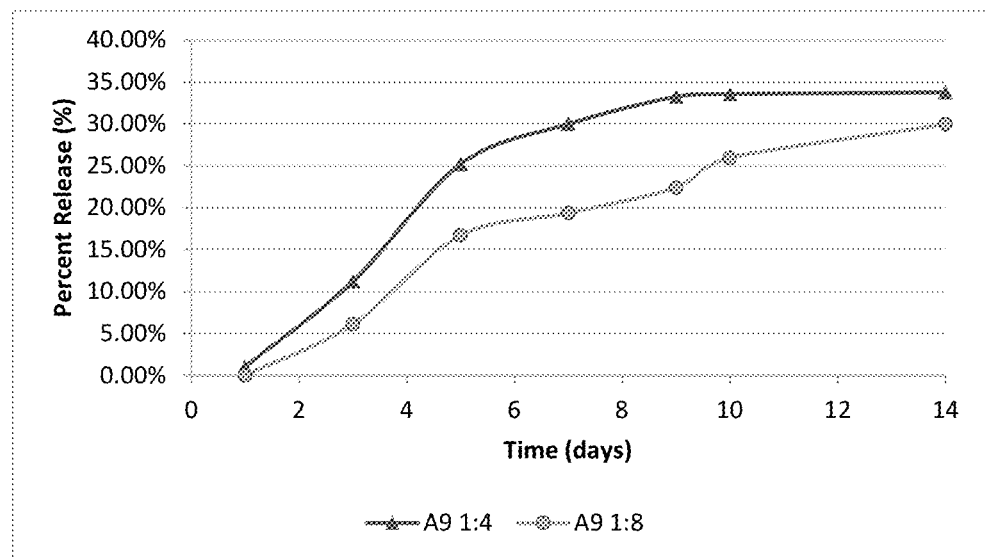
FIG. 1 shows cumulative % release for liraglutide from liraglutide-A9.

The following description sets forth exemplary methods, parameters and the like. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polyaminoacid" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

As used herein, the term "about" refers to a value or parameter that includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. For example, when used in the context of quantitative measurements, the term "about" would refer to the indicated amount ±10%, ±5% or ±1%. Also, to the term "about X" includes description of "X".

Peptides

The present disclosure provides new peptides useful for controlled release of pharmaceutically active compounds, such as those having a log P value of less than 4. The peptides have a specific pattern of acidic, basic and neutral amino acids which imparts the unique and surprising controlled release of the pharmaceutically active compound. In a preferred embodiment, the peptide includes a primarily acidic peptide fragment, a primarily basic peptide fragment, and between them a more neutral peptide fragment. Without being bound by theory, it is contemplated that the peptides, by virtue of their inclusion of both acidic fragments and basic fragments, can interact with each other and form a nano or micro structure. Such a nano or micro structure can encapsulate or otherwise associate a drug molecule, which encapsulation or association modulates the absorption, release, or clearance of the drug molecule in a subject.

The peptide, comprising a combination of acidic, neutral and basic amino acids, can be non-covalently bonded with or used in combination with the pharmaceutically active compound so as to allow for controlled release delivery of the pharmaceutically active compound.

In one embodiment, this disclosure provides a peptide of formula I':

$$B'—U'—B—U—W—U'—W', \qquad I'$$

wherein:
each of B, B', W and W' independently is a peptide comprising at least 75% acidic amino acids or 75% basic amino acids, provided that when B is a peptide having at least 75% acidic amino acids, W is a peptide having at least 75% basic amino acids or vice versa;
each of U and U' independently is a peptide comprising neutral amino acids;
each of B, U and W independently comprises 2 to 9 amino acids; and
each of B', U' and W' independently comprises 2 to 9 amino acids or the adjacent U' and W' are absent or the adjacent B' and U' are absent or all B', U' and W' are absent; provided that the peptide of formula I' comprises from about 9 to 21 amino acids.

In one embodiment, this disclosure provides a peptide of formula I', wherein U and U' are the same. In another embodiment, W and W' are the same. In another embodiment, B and B' are the same. In another embodiment, U and U' are the same and W and W' are the same. In another embodiment, B and B' are the same, U and U' are the same and W and W' are the same. In another embodiment, adjacent U' and W' are absent. In another embodiment, adjacent B' and U' are absent. In another embodiment, all B', U' and W' are absent.

In another embodiment, this disclosure provides a peptide of formula I:

$$B—U—W, \qquad I$$

wherein:
each of B and W independently is a peptide comprising at least 75% acidic amino acids or 75% basic amino acids, provided that when B is a peptide having at least 75% acidic amino acids, W is a peptide having at least 75% basic amino acids or vice versa;
U is a peptide comprising neutral amino acids; and
each of B, U and W independently comprises 2 to 9 amino acids, provided that the peptide of formula I comprises from about 9 to 21 amino acids.

In some embodiments, the acidic amino acids are independently selected from aspartic acid or glutamic acid. In some embodiments, the basic amino acids are independently selected from lysine, arginine or histidine. In some embodiments, the neutral amino acids are independently selected from tryptophan, phenylalanine, glycine, alanine, valine, isoleucine, leucine, serine, threonine, tyrosine, asparagine, glutamine, and proline. In some embodiments, B or B' does not include cysteine or methionine. In some embodiments, W or W' does not include cysteine or methionine. In some embodiments, U or U' does not include cysteine or methionine. In some embodiment, the peptide does not include cysteine or methionine.

In some embodiments, B comprises at least 75% (or at least 80%, 85%, or 90%) acidic amino acids and remaining neutral amino acids and W comprises at least 75% (or at least 80%, 85%, or 90%) basic amino acids and remaining neutral amino acids or vice versa. In some embodiments, B comprises 100% acidic amino acids and W comprises 100% basic amino acids or vice versa. In some embodiments, all but one (being neutral) of the amino acids of B are acidic amino acids. In some embodiments, all but two (being neutral) of the amino acids of B are acidic amino acids. In some embodiments, all but one (being neutral) of the amino acids of W are basic amino acids. In some embodiments, all but two (being neutral) of the amino acids of W are basic amino acids.

In some embodiments, B' comprises at least 75% (or at least 80%, 85%, or 90%) acidic amino acids and remaining neutral amino acids and W' comprises at least 75% (or at least 80%, 85%, or 90%) basic amino acids and remaining neutral amino acids or vice versa. In some embodiments, B' comprises 100% acidic amino acids and W' comprises 100% basic amino acids or vice versa. In some embodiments, all but one (being neutral) of the amino acids of B' are acidic amino acids. In some embodiments, all but two (being neutral) of the amino acids of B' are acidic amino acids. In some embodiments, all but one (being neutral) of the amino acids of W' are basic amino acids. In some embodiments, all but two (being neutral) of the amino acids of W' are basic amino acids.

In some embodiments, all amino acids of U or U' are neutral. In some embodiments, U or U' includes a single acidic or basic amino acid.

The peptides, in some embodiments, include at least 9 amino acids. In some embodiments, the peptides include at least 10, 11, 12, 13, 14, 15, 16, 17, 18, 19 or 20 amino acids. In some embodiments, the peptides include no more than 25, 24, 23, 22, 21, 20, 19, 18, 17, 16 or 15 amino acids. In some embodiments, the peptides include no more than 21 amino acids.

In some embodiments, each of B, B', U, U', W and W' independently comprises from 2 to 9 amino acids. In some embodiments, each of B, B', U, U', W and W' independently comprises equal number of amino acids. In some embodiments, each of B, B', U, U', W and W' independently comprises 3 amino acids. In some embodiments, adjacent U' and W' are absent. In another embodiment, adjacent B' and U' are absent. In another embodiment, all B', U' and W' are absent.

In some embodiments, the peptide of formula I is RRRRRRLLLAAAEEE (SEQ ID NO: 2), RRRRRRLL-LAAAEEE (SEQ ID NO: 2), KKKKKKLLLAAAEEE (SEQ ID NO: 3), RRRRRLLLAAAEE (SEQ ID NO: 4), RRRLLLEEE (SEQ ID NO: 5), RRRRRLLLEEEEE (SEQ ID NO: 6), RRRRRLLLLLEEEEE (SEQ ID NO:1), RRRRRRLLLLLLEEEEEEE (SEQ ID NO: 16), EEEEELLLLLRRRRR (SEQ ID NO: 7), or RRRRRLLLLLDDDDD (SEQ ID NO: 8).

In some embodiments, the peptide of formula I' is RRRRRRLLLLLLEEEEEE (SEQ ID NO: 16).

Mixtures and Compositions

Compositions are also provided, in some embodiments, which include a peptide of the disclosure and a pharmaceutically active compound. The peptide may be non-covalently bonded with or used in combination with the pharmaceutically active compound so as to allow for controlled release delivery of the pharmaceutically active compound.

In some embodiments, the composition further comprises a solvent. In certain embodiments, the solvent is tetrahydrofuran, dimethylformamide, dimethylsulfoxide or acetonitrile.

The disclosed compositions and methods are useful for controlled delivery of any pharmaceutically active agent. In some embodiments, the compositions and methods are particularly useful for pharmaceutically active compounds having a log P (partition coefficient) value of less than 4. In some embodiments, the log p value is from about 1 to 2 or from about 2 to 3 or from about 3 to less than 4. In some embodiments, the log p value is from about −1 to −2 or from about −2 to −3 or from about −3 to less than −4. In some embodiments, the log p value is from about −4 to 4 or from about −3 to 3 or from about −2 to 2 or from about −1 to less than 1.

As used herein, the term "log P value" is calculated as the log of the measured octanol-water partition coefficient of a pharmaceutically active agent at the room temperature.

The term "partition coefficient" refers to the ratio of concentrations of a compound in a mixture of two immiscible phases at equilibrium. This ratio is therefore a measure of the difference in solubility of the compound in these two phases. Typically, one of the phases is in a solvent like water while the second is hydrophobic. Hence the partition coefficient measures how hydrophilic or hydrophobic a chemical substance is. Partition coefficients are useful in estimating the distribution of drugs within the body. Hydrophobic drugs with high octanol/water partition coefficients are mainly distributed to hydrophobic areas such as lipid bilayers of cells. Conversely hydrophilic drugs (low octanol/water partition coefficients) are found primarily in aqueous regions such as blood serum.

The release of the pharmaceutically active compounds can be controlled in a number of different ways including, but not limited to, by varying the weight ratio of the pharmaceutically active compound to the peptide. In some embodiments, the composition comprises a weight ratio of the pharmaceutically active compound to the peptide from about 1:0.1 to about 1:100 or from about 1:1 to about 1:80 or from about 1:3 to about 1:20. In some embodiments, the weight ratio is about 1:0.5 to about 1:12. In some embodiments, the weight ratio is about 1:0.5, about 1: 0.7, about 1:1, about 1:2, about 1:3, about 1:4, about 1:5, about 1:6, about 1:7, about 1:8, about 1:9, about 1:10, about 1:11, about 1:12, about 1:13, about 1:14, about 1:15, about 1:20, about 1:25, about 1:35, about 1:45, about 1:60, about 1:75, about 1:90 or about 1:100.

In some embodiments, the composition comprises a mole ratio of the pharmaceutically active compound to the peptide from about 1:0.1 to about 1:20 or from about 1:0.5 to about 1:8 or from about 1:0.75 to about 1:7. In some embodiments, the mole ratio is about 1:1 to about 1:8. In some embodiments, the mole ratio is about 1:0.5, about 1:0.7, about 1:1, about 1:2, about 1:3, about 1:4, about 1:5, about 1:6, about 1:7, about 1:8, about 1:9, about 1:10 or about 1:20.

In some embodiments, the release of the pharmaceutically active compound is controlled by adjusting weight ratio of the pharmaceutically active compound to the peptide of formula I.

In some embodiments, this disclosure provides a composition as described herein, wherein the peptide self organizes around the pharmaceutically active compound. In some embodiments, the compound of formula I self organizes around the pharmaceutically active compound via intramolecular and/or intermolecular stacking. In some embodiments, the compound of formula I and the pharmaceutically active compound are stacked through non-covalent bonding.

In one embodiment, the pharmaceutically active compound is an analgesic agent, an anesthetic agent, an anti-asthmatic agent, an antibiotic, an anti-depressant agent, an anti-diabetic agent, an anti-fungal agent, an anti-hypertensive agent, an anti-inflammatory agent, an anti-neoplastic agent, an anxiolytic agent, an immunostimulating agent or an immunosuppressive agent. In some embodiments, the pharmaceutically active compound is an anti-diabetic agent.

In some embodiments, the pharmaceutically active compound is a small molecule. In some embodiments, the pharmaceutically active compound is a large molecule. In some embodiments, the large molecule is selected from antibody, peptide, nanobody, antibody fragments, FAB fragment, affibody, protein, nucleotide and trinectin derivatives. In some embodiments, the large molecule is a protein or a nucleotide.

Proteins useful in the disclosed complexes and compositions include, for example, molecules such as cytokines and their receptors, as well as chimeric proteins comprising cytokines or their receptors, including, for example tumor necrosis factor alpha and beta, their receptors and their derivatives; renin; growth hormones, including human growth hormone (e.g., rhGH), bovine growth hormone, methione-human growth hormone, des-phenylalanine human growth hormone, and porcine growth hormone; growth hormone releasing factor (GRF); octreotide, parathyroid and pituitary hormones; thyroid stimulating hormone; human pancreas hormone releasing factor; lipoproteins; colchicine; prolactin; corticotrophin; thyrotropic hormone; oxytocin; vasopressin; somatostatin; lypressin; pancreozymin; leuprolide; alpha-1-antitrypsin; insulin; insulin analogs; insulin derivatives; insulin prodrugs; glargine; insulin A-chain; insulin B-chain; proinsulin; follicle stimulating hormone; calcitonin; luteinizing hormone; luteinizing hormone releasing hormone (LHRH); LHRH agonists and antagonists; glucagon; clotting factors such as factor VIIIC, factor IX, tissue factor, and von Willebrands factor; anti-clotting factors such as Protein C; atrial natriuretic factor; lung surfactant; a plasminogen activator other than a tissue-type plasminogen activator (t-PA), for example a urokinase; bombesin; thrombin; hemopoietic growth factor; enkephalinase; RANTES (regulated on activation normally T-cell expressed and secreted); human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; chorionic gonadotropin; gonadotropin releasing hormone; bovine somatotropin; porcine somatotropin; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as acidic FGF and basic FGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha (e.g., interferona2A or interferona2B), -beta, -gamma, -lambda and consensus interferon; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV-1 envelope glycoprotein, gp120, gp160 or fragments thereof; transport proteins; homing receptors; addressins; fertility inhibitors such as the prostaglandins; fertility promoters; regulatory proteins; antibodies and chimeric proteins, such as immunoadhesins; precursors, derivatives, prodrugs and analogues of these compounds, and pharmaceutically acceptable salts of these compounds, or their precursors, derivatives, prodrugs and analogues.

Suitable proteins or peptides are synthetic or native or recombinant and include, e.g., fusion proteins. In some embodiments, the protein is a growth hormone, such as recombinant human growth hormone (rhGH, insulin, insulin A-chain, insulin B-chain, and proinsulin; or a growth factor, such as vascular endothelial growth factor (VEGF), nerve growth factor (NGF), platelet-derived growth factor (PDGF), fibroblast growth factor (FGF), epidermal growth factor (EGF), transforming growth factor (TGF), and insulin-like growth factor-I and -II (IGF-I and IGF-II).

Nucleic acid pharmaceutically active agents include nucleic acids as well as precursors, derivatives, prodrugs and analogues thereof, e.g., therapeutic nucleotides, nucleosides and analogues thereof; therapeutic oligonucleotides; and therapeutic polynucleotides. Pharmaceutically active agents selected from this group may find particular use as anticancer agents and antivirals. Suitable nucleic acid pharmaceutically active agents may include for example ribozymes, antisense oligodeoxynucleotides, aptamers and siRNA. Examples of suitable nucleoside analogues include, but are not limited to, cytarabine (araCTP), gemcitabine (dFdCTP), and floxuridine (FdUTP).

A variety of other pharmaceutically active agents may be used in the compositions disclosed herein. Suitable compounds include, but are not limited to, compounds directed to one or more of the following drug targets: kringle domain, carboxypeptidase, carboxylic ester hydrolases, glycosylases, rhodopsin-like dopamine receptors, rhodopsin-like adrenoceptors, rhodopsin-like histamine receptors, rhodopsin-like serotonin receptors, rhodopsin-like short peptide receptors, rhodopsin-like acetylcholine receptors, rhodopsin-like nucleotide-like receptors, rhodopsin-like lipid-like ligand receptors, rhodopsin-like melatonin receptors, metalloprotease, transporter ATPase, carboxylic ester hydrolases, peroxidase, lipoxygenase, DOPA decarboxylase, A/G cyclase, methyltransferases, sulphonylurea receptors, other transporters (e.g., dopamine transporter, GABA transporter 1, norepinephrine transporter, potassium-transporting ATPase α-chain 1, sodium-(potassium)-chloride cotransporter 2, serotonin transporter, synaptic vesicular amine transporter, and thiazide-sensitive sodium-chloride cotransporter), electrochemical nucleoside transporter, voltage-gated ion channels, GABA receptors (Cys-Loop), acetylcholine receptors (Cys-Loop), NMDA receptors, 5-HT3 receptors (Cys-Loop), ligand-gated ion channels Glu: kainite, AMPA Glu receptors, acid-sensing ion channels aldosterone, ryanodine receptors, vitamin K epoxide reductase, MetGluR-like $GABA_B$ receptors, inwardly rectifying $K^+$ channel, NPC1L1, MetGluR-like calcium-sensing receptors, aldehyde dehydrogenases, tyrosine 3-hydroxylase, aldose reductase, xanthine dehydrogenase, ribonucleoside reductase, dihydrofolate reductase, imp dehydrogenase, thioredoxin reductase, dioxygenase, inositol monophosphatase, phosphodiesterases, adenosine deaminase, peptidylprolyl isomerases, thymidylate synthase, aminotransferases, farnesyl diphosphate synthase, protein kinases, carbonic anhydrase, tubulins, troponin, inhibitor of IκB kinase-β, amine oxidases, cyclooxygenases, Cytochrome P450s, thyroxine 5-deiodinase, steroid dehydrogenase, HMG-CoA reductase, steroid reductases, dihydroorotate oxidase, epoxide hydrolase, transporter ATPase, translocator, glycosyltransferases, nuclear receptors NR3 receptors, nuclear receptors: NR1 receptors, and topoisomerase.

In some embodiments, the pharmaceutically active agent is a compound targeting one of rhodopsin-like GPCRs, nuclear receptors, ligand-gated ion channels, voltage-gated ion channels, penicillin-binding protein, myeloperoxidase-like, sodium: neurotransmitter symporter family, type II DNA topoisomerase, fibronectin type III, and cytochrome P450.

In some embodiments, the pharmaceutically active agent is an anticancer agent where most of the active agent has a log P value of about 2. Suitable anticancer agents include, but are not limited to, actinomycin d, alemtuzumab, allopurinol sodium, altretamine, amsacrine, anastrozole, Ara-CMP, asparaginase, azacytadine, bendamustine, bevacizumab, bicalutimide, bleomycin (e.g., bleomycin A2 and B2), bortezomib, busulfan, camptothecin sodium salt, capecitabine, carboplatin, carmustine, cetuximab, chlorambucil, cisplatin, cladribine, clofarabine, cyclophosphamide, cytarabine, dacarbazine, dactinomycin, daunorubicin, daunorubicin liposomal, dacarbazine, decitabine, docetaxel, doxorubicin, doxorubicin liposomal, epirubicin, estramustine, etoposide, etoposide phosphate, exemestane, floxuridine, fludarabine, fluadarabine phosphate, 5-fluorouracil, fotemustine, fulvestrant, gemcitabine, goserelin, hexamethylmelamine, hydroxyurea, idarubicin, ifosfamide, imatinib, irinotecan, ixabepilone, lapatinib, letrozole, leuprolide acetate, lomustine, mechlorethamine, melphalan, 6-mercaptopurine, methotrexate, mithramycin, mitomycin c, mitotane, mitoxantrone, nimustine, ofatumumab, oxaliplatin, paclitaxel, panitumumab, pegaspargase, pemetrexed, pentostatin, pertuzumab, picoplatin, pipobroman, plerixafor, procarbazine, raltitrexed, rituximab, streptozocin, temozolomide, teniposide, 6-thioguanine, thiotepa, topotecan, trastuzumab, treosulfan, triethylenemelamine, trimetrexate, uracil nitrogen mustard, valrubicin, vinblastine, vincristine, vindesine, vinorelbine, and analogues, precursors, derivatives and pro-drugs thereof. It should be noted that two or more of the above compounds may be used in combination in the compositions of the present disclosure.

Pharmaceutically active agents of interest for use in the disclosed compositions may also include opioids and derivatives thereof as well as opioid receptor agonists and antagonists, e.g., methadone, naltrexone, naloxone, nalbuphine, fentanyl, sufentanil, oxycodone, oxymorphone, hydrocodone, hydromorphone, and pharmaceutically acceptable salts and derivatives thereof.

In some embodiments, the pharmaceutically active agent is mostly hydrophilic with log P value of about 1. Examples include peptides, protein and nucleotides. Suitable peptides for use as the complexes and compositions disclosed herein include, but are not limited to, exenatide and glucagon-like peptide-1 (GLP-1) and precursors, derivatives, prodrugs and analogues thereof. Some specific examples include, but are not limited to, liraglutide, lixisenatide, albiglutide, dulaglutide and semaglutide. Also, some pharmaceutically active agent is 'small-molecule' with molecular weights between 200-2000 Da and log P value less than 4. This 'small molecule' class includes prostacyclin based drugs such as epoprostanol.

In some embodiments, the pharmaceutically active compound is a small molecule. In some embodiments, the peptide of formula I is RRRRRLLLLLEEEEE (A9) (SEQ ID NO:1). In some embodiments, pharmaceutically active compound is liraglutide, insulin or ropivacaine metabolite. In some embodiments, the weight ratio of the pharmaceutically active compound to A9 is in a range of about 1:0.1 to about 1:20. In some embodiments, the weight ratio of the pharmaceutically active compound to A9 is in a range of about 1:2 to about 1:20.

In some embodiments the pharmaceutically active agent is a low molecular weight compound, e.g., a compound having a molecular weight of less than or equal to about 800 Daltons, e.g., less than or equal to about 500 Daltons. In some embodiments, the pharmaceutically active agent is a compound having a molecular weight ranging from 800 Daltons to 100 Daltons, e.g., 700 Daltons to 200 Daltons, 600 Daltons to 300 Daltons, or 500 Daltons to 400 Daltons.

In some embodiments, the pharmaceutically active agent comprises at least one member selected from a peptide, protein, and small molecule, the small molecule having a molecular weight less than 500 Daltons.

The pharmaceutically active agent may contain one functional group that is interactable to the peptide of formula I. The pharmaceutically active agent may contain more than one functional group that is capable of forming non-covalent bonds with the peptide of formula I.

In some embodiments, the pharmaceutically active agent is stable in water. For instance, when the pharmaceutically active agent is placed in water at 25° C. for 1 hour, 12 hours, or 24 hours, the purity of the pharmaceutically active agent is degraded less than 5%, such as less than 3% or less than 2%.

The pharmaceutically active agent or pharmaceutically active agent complex may be present in any suitable concentration in the compositions disclosed herein. Suitable concentrations may vary depending on the potency of the pharmaceutically active agent, pharmacokinetic half-life, etc. For example, the pharmaceutically active agent may be present in a range of from about 1% to about 50% by weight of the composition, e.g., from about 5% to about 45%, from about 10% to about 40%, from about 15% to about 35%, or from about 20% to about 30% by weight of the composition. The complex including the pharmaceutically active agent may be present at a concentration ranging from about 10 mg/mL to about 500 mg/mL, such as from about 50 mg/mL to about 450 mg/mL, about 100 mg/mL to about 400 mg/mL, about 150 mg/mL to about 350 mg/mL, or about 200 mg/mL to about 300 mg/mL.

In some embodiments, the composition is in a unit dosage form. Examples of the unit dosage form include, but are not limited to, tablets, capsules, oral solutions, oral suspensions, sprays, patches, sachets, inhaled as powders, sublingual tabs, nasal sprays. On the injection side, injected via intravenous infusion, sub-dermal, intra-muscular and subcutaneous injections.

Delivery Methods

The present disclosure also provides controlled release delivery methods of pharmaceutically active compounds by using the peptides described herein. The rate of dissolution of pharmaceutically active compounds can be reduced by non-covalently bonding it with or using in combination with a peptide of formula I as described herein. Further, the release rate of the pharmaceutically active compound can be controlled by adjusting the appropriate level of the peptide. Control delivery and duration of delivery of pharmaceutically active agents mostly depend on the higher weight or molar ratios of the peptide of formula I to the active agent.

In some embodiments, a composition for controlled release is prepared by mixing a pharmaceutically active compound and a peptide of formula I in a solvent as described in the examples. In some embodiments, separate solutions of the pharmaceutically active compound and the peptide of formula I can be prepared and then combined before the administration, or are administered simultaneously or within a certain amount of time, to a subject in need thereof.

In one embodiment, this disclosure provides a drug delivery method comprising administering to a subject in need thereof a composition comprising:
 i) a pharmaceutically active compound having a log P value of less than 4; and
 ii) a peptide of formula I':

wherein:
 each of B, B', W and W' independently is a peptide comprising at least 75% acidic amino acids or 75% basic amino acids, provided that when B is a peptide having at least 75% acidic amino acids, W is a peptide having at least 75% basic amino acids or vice versa;
 each of U and U' independently is a peptide comprising neutral amino acids;
 each of B, U and W independently comprises 2 to 9 amino acids; and
 each of B', U' and W' independently comprises 2 to 9 amino acids or the adjacent U' and W' are absent or the adjacent B' and U' are absent or all B', U' and W' are absent; provided that the peptide of formula I' comprises from about 9 to 21 amino acids.

In one embodiment, this disclosure provides a drug delivery method comprising administering to a subject in need thereof a composition comprising:
 i) a pharmaceutically active compound having a log P value of less than 4; and
 ii) a peptide of formula I:

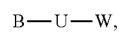

wherein:
 each of B and W independently is a peptide comprising at least 75% acidic amino acids or 75% basic amino acids, provided that when B is a peptide having at least 75% acidic amino acids, W is a peptide having at least 75% basic amino acids or vice versa;
 U is a peptide comprising neutral amino acids; and
 each of B, U and W independently comprises 2 to 9 amino acids, provided that the peptide of formula I comprises from about 9 to 21 amino acids.

In some embodiments, the drug delivery method comprises a composition as described herein. In some embodiments, the drug delivery method comprises administering a composition to a subject in need thereof by oral, intravenous, subcutaneous, intraperitoneal, intrathecal, intramuscular, intravitreal, intracranial, nasal, topical or transdermal route. In some embodiments, the method delivers the composition by oral route.

In some embodiments, the method comprises administering a pharmaceutically active compound which is an analgesic agent, an anesthetic agent, an anti-asthmatic agent, an antibiotic, an anti-depressant agent, an anti-diabetic agent, an anti-fungal agent, an anti-hypertensive agent, an anti-inflammatory agent, an anti-neoplastic agent, an anxiolytic agent, an immunostimulating agent or an immunosuppressive agent.

In some embodiments, the unit dosage form is packed in a delivery device. In some embodiments, the delivery device is a syringe or a catheter.

EXAMPLES

Example 1: Preparation of Peptides of Formula I

The peptides of formula I were prepared by the following method. The synthesis was done on a polystyrene resin with Wang linker in an ABI 431A peptide synthesizer. FastMoc chemistry used HBTU/Oxyma as activation reagent; 20% piperidine as Fmoc (9-fluorenylmethoxycarbonyl) deprotection reagent. Amino acid reagents were protected at the amine with Fmoc, and on the side chains with standard protecting groups.

Cleavage and deprotection were effected simultaneously over 2 hours in TFA/Water/TIS (95:2.5:2.5) followed by precipitation in ethyl ether three times.

The crude peptide precipitate was purified by reversed phase on a Higgins Proto 200 C18 column with a gradient of 20 to 40% acetonitrile containing 0.1% TFA.

The peptides, RRRRRRLLLAAAEEE (A3) (SEQ ID NO: 2), RRRRRRLLLAAAEEE (A4) (SEQ ID NO: 2), KKKKKKLLLAAAEEE (A5) (SEQ ID NO: 3), RRRRRLLLAAAEE (A6) (SEQ ID NO: 4), RRRLLLEEE (A7) (SEQ ID NO: 5), RRRRRLLLEEEEE (A8) (SEQ ID NO: 6), RRRRRLLLLLEEEEE (A9) (SEQ ID NO:1), and RRRRRLLLLLDDDDD (A10) (SEQ ID NO: 8), were prepared using the method described above.

Also, the peptides RRREEE (A11) (SEQ ID NO: 9), LLLEEE (A12) (SEQ ID NO: 10), RRRLLL (A13) (SEQ ID NO: 11), RRRRREEEEE (A14) (SEQ ID NO: 12), LLLLLRRRRR (A15) (SEQ ID NO: 13), RRRLLLEEELLLRRR (A16) (SEQ ID NO: 14), RRRRRRRLLLLLLLEEEEEEE (A17) (SEQ ID NO: 16), EEEEELLLLLRRRRR (A18) (SEQ ID NO: 7), and RRRRRRREEEEEEE (A19) (SEQ ID NO: 15) were prepared using the same method as described above.

Example 2. Preparation and In Vitro Analysis of Liraglutide with A9

10 mg of liraglutide were placed in a 20 mL sintered glass vial. Different ratio of liraglutide and A9 were added, with 1:4 weight ratio or 1:8 weight ratio of liraglutide:A9, with 100 uL of dimethyl sulfoxide and the mixture was stirred at 100 rpm for 5 min at 37° C. (until it became a visibly clear solution) to provide Liraglutide-A9.

Liraglutide in Diluent (Control)

10 mg of liraglutide were placed in a 20 mL sintered glass vial and 100 uL of dimethyl sulfoxide or dimethyl formamide were added and the mixture was stirred at 100 rpm for 5 min at 37° C. (until it became a visibly clear solution).

In Vitro Analysis of Liraglutide Release

Dissolution experiments were conducted as set forth below to determine the in vitro release of liraglutide from liraglutide-A9 prepared above.

For dissolution or in vitro release testing, PBS (phosphate buffered saline) pH of about 7.4 was used as the medium, and the solutions of liraglutide was dispersed into the dissolution medium. For the dissolution study, a known amount of liraglutide (20 uL of above solution contains 2 mg of liraglutide) was placed into 2 mL conical shaped polypropylene vials. 1 mL release medium (0.01M PBS at pH 7.4 equilibrated at 37° C.) was added gently to each vial such that the surface of the formulation was not disturbed. The samples were placed at 37° C./100 rpm in an orbital shaker. At every time point essentially all the release medium was removed and replaced by fresh solution. The amount of liraglutide in solution at each time point was determined by HPLC.

Results

Figure 20:
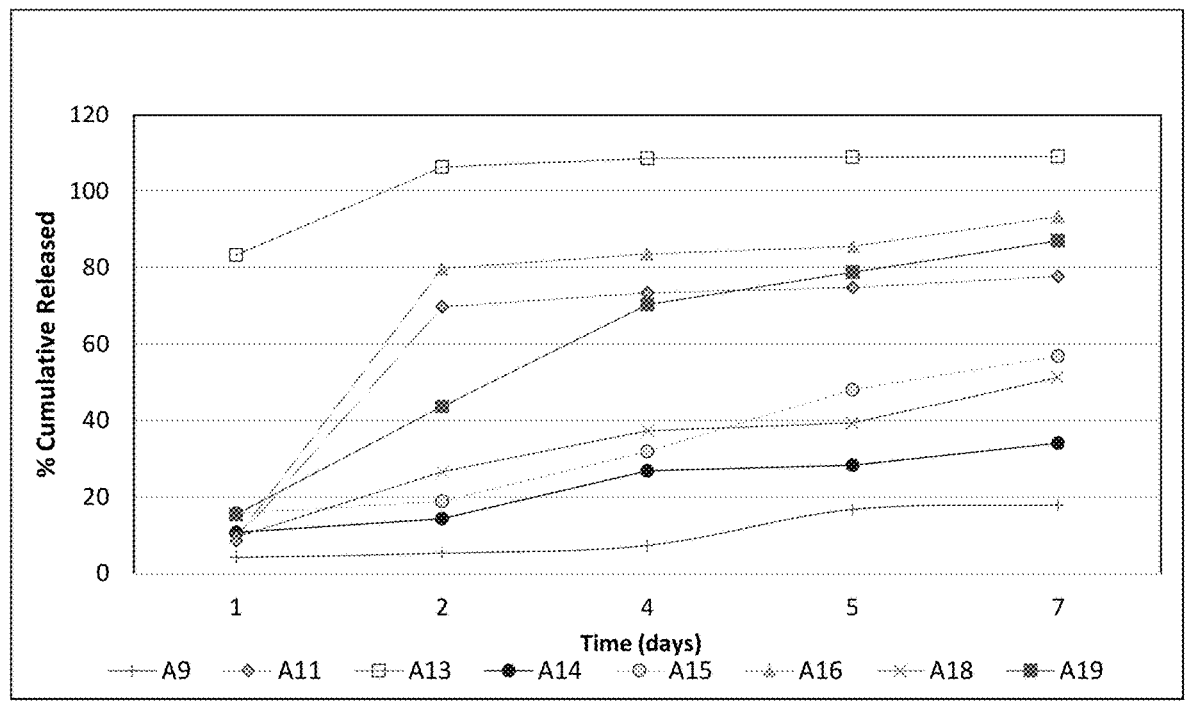
FIG. 20 shows the % cumulative release of liraglutide from liraglutide-A9, liraglutide-A11, liraglutide-A13, liraglutide-A14, liraglutide-A15, liraglutide-A16, liraglutide-A18 and liraglutide-A19.

The in vitro dissolution profile for liraglutide from liraglutide-A9 (with a 1:4 weight ratio and 1:8 weight ratio) is plotted in FIG. 1. The in vitro release of liraglutide showed more controlled release when liraglutide to A9 ratio is 1:8 whereas 1:4 showed more initial release. The in vitro dissolution profiles for liraglutide from liraglutide-A9, liraglutide-A11, liraglutide-A13, liraglutide-A14, liraglutide-A15, liraglutide-A16, liraglutide-A18, liraglutide-A19 are plotted in FIG. 20.

Example 3. Preparation and In Vitro Analysis of Insulin with A6, A8 or A9

10 mg of rh-Insulin were placed in a 20 mL sintered glass vial. Different ratio of insulin and A6 were added, with 1:5 weight ratio or 1:10 weight ratio of insulin to A6, with 100 uL of dimethyl sulfoxide and the mixture was stirred at 100 rpm for 5 min at 37° C. (until it became a visibly clear solution), to provide insulin-A6.

Using the same procedure as above, insulin with A8 were prepared with a 1:4 weight ratio or 1:8 weight ratio of insulin:A8, to provide insulin-A8.

Using the same procedure as above, insulin with A9 were prepared with a 1:4 weight ratio or 1:8 weight ratio of insulin:A9, to provide insulin-A9.

rh-Insulin in Diluent (Control)

10 mg of Insulin was placed in a 20 mL sintered glass vial and 100 uL of dimethyl sulfoxide or dimethyl formamide were added and the mixture was stirred at 100 rpm for 5 min at 37° C. (until it became a visibly clear solution).

In Vitro Analysis of Insulin Release

Dissolution experiments were conducted as set forth below to determine the in vitro release of insulin from insulin-A6, insulin-A8 and insulin-A9 prepared above.

For dissolution or in vitro release testing, PBS (Phosphate buffered saline) pH of about 7.4 was used as the medium, and the solutions of insulin was dispersed into the dissolution medium. For the dissolution study, a known amount of insulin (20 uL of above solution contains 2 mg of insulin) was placed into 2 mL conical shaped polypropylene vials. 1 mL release medium (0.01 M PBS at pH 7.4 equilibrated at 37° C.) was added gently to each vial such that the surface of the formulation was not disturbed. The samples were placed at 37° C./100 rpm in an orbital shaker. At every time point essentially all the release medium was removed and replaced by fresh solution. The amount of Insulin in solution at each time point was determined by HPLC.

Results

Figure 2:
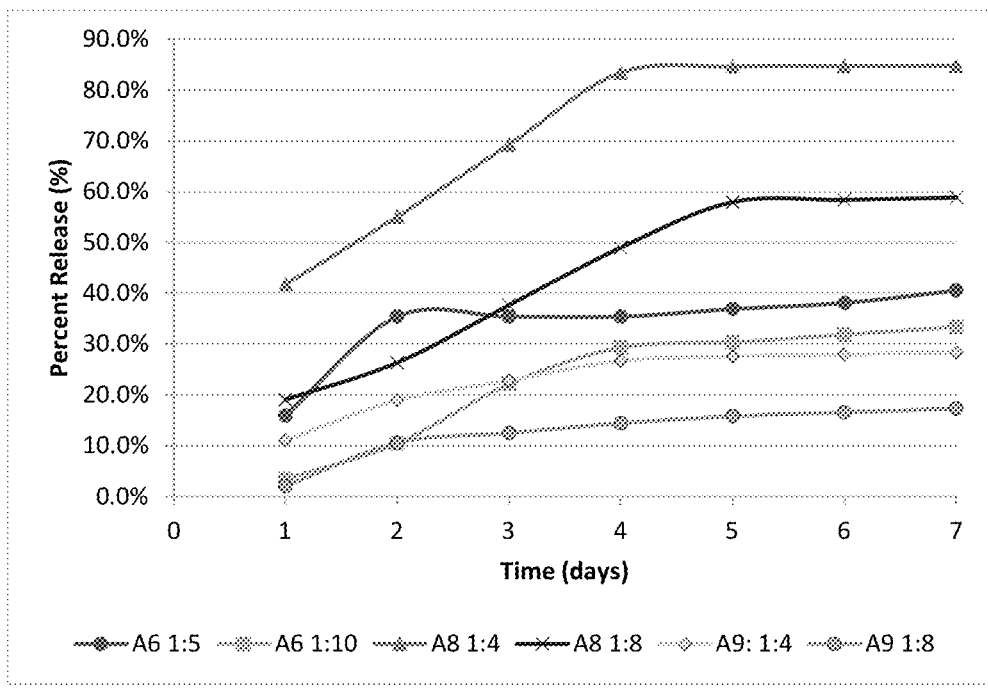
FIG. 2 shows cumulative % release for rh-insulin from insulin-A6, insulin-A8 and insulin-A9.

The in vitro dissolution profile for rh-insulin from insulin-A6 (with a 1:5 weight ratio and 1:10 weight ratio of insulin:A6), insulin-A8 (with a 1:4 weight ratio and 1:8 weight ratio of insulin:A8) and insulin-A9 (with a 1:4 weight ratio and 1:8 weight ratio of insulin:A9) is plotted in FIG. 2. The results indicate that the % release of insulin is slower with higher weight ratio of each peptide such as A6, A8 and A9.

Example 4. Preparation and In Vitro Analysis of Insulin Glargine with A9

10 mg of insulin glargine were placed in a 20 mL sintered glass vial. Different ratio of insulin glargine and A9 were added, with 1:4 weight ratio or 1:8 weight ratio of insulin glargine to A9, with 100 uL of dimethyl sulfoxide and the mixture was stirred at 100 rpm for 5 min at 37° C. (until it became a visibly clear solution), to provide insulin glargine-A9.

Insulin Glargine in Diluent (Control)

10 mg of insulin glargine was placed in a 20 mL sintered glass vial and 100 uL of dimethyl sulfoxide or dimethyl formamide and the mixture was stirred at 100 rpm for 5 min at 37° C. (until it became a visibly clear solution).

In Vitro Analysis of Insulin Release

Dissolution experiments were conducted as set forth below to determine the in vitro release of insulin glargine from the insulin glargine-A9 prepared above.

For dissolution or in vitro release testing, PBS (Phosphate buffered saline) pH of about 7.4 was used as the medium, and the solutions of Insulin glargine was dispersed into the dissolution medium. For the dissolution study, a known amount of Insulin glargine (20 uL of above solution contains 2 mg of insulin glargine) was placed into 2 mL conical shaped polypropylene vials. 1 mL release medium (0.01M PBS at pH 7.4 equilibrated at 37° C.) was added gently to each vial such that the surface of the formulation was not disturbed. The samples were placed at 37° C./100 rpm in an orbital shaker. At every time point essentially all the release medium was removed and replaced by fresh solution. The amount of insulin glargine in solution at each time point was determined by HPLC.

Results

Figure 3:
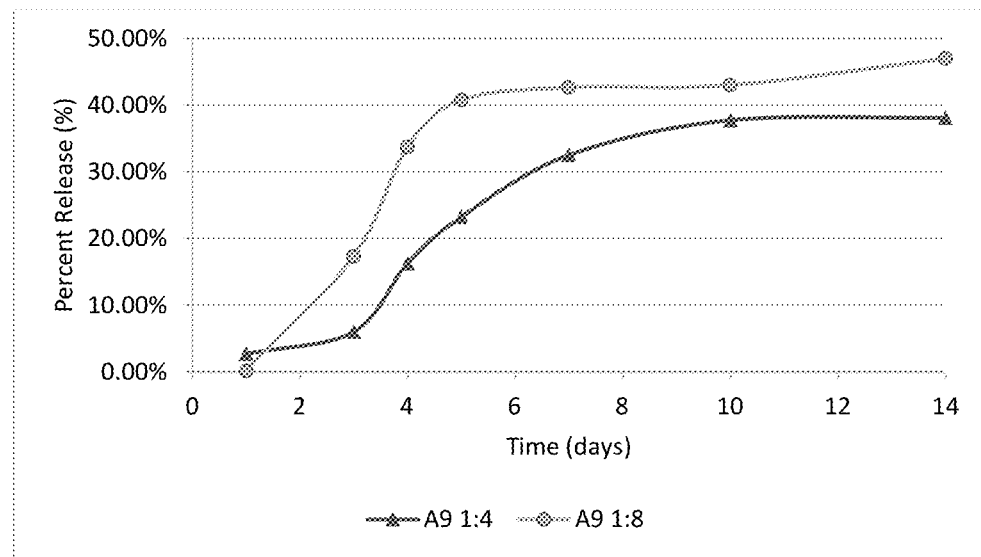
FIG. 3 shows cumulative % release for insulin glargine from insulin glargine-A9.

The in vitro dissolution profile for insulin glargine from insulin glargine-A9 (with a 1:4 weight ratio and 1:8 weight ratio of insulin glargine:A9) is plotted in FIG. 3. Insulin glargine released less with 1:4 ratio with A9 compared to ratio 1:8.

Example 5. Preparation and In Vitro Analysis of Liraglutide/Insulin Combo with A9

10 mg each of insulin and liraglutide were placed in a 20 mL sintered glass vial. A9 was added with 1:5 weight ratio to insulin and liraglutide, with 100 uL of dimethyl sulfoxide and the mixture was stirred at 100 rpm for 5 min at 37° C. (until it became a visibly clear solution), to provide insulin/liraglutide-A9.

For dissolution or in vitro release testing, PBS (Phosphate buffered saline) pH of about 7.4 was used as the medium, and the solutions of liraglutide, Insulin combo solution was dispersed into the dissolution medium. For the dissolution study, a known amount of Insulin and liraglutide (20 uL of above solution contains 2 mg of Insulin and liraglutide) was placed into 2 mL conical shaped polypropylene vials. 1 mL release medium (0.01M PBS at pH 7.4 equilibrated at 37° C.) was added gently to each vial such that the surface of the formulation was not disturbed. The samples were placed at 37° C./100 rpm in an orbital shaker. At every time point essentially all the release medium was removed and replaced by fresh solution. The amount of Insulin and liraglutide in solution at each time point was determined by HPLC.

Results

Figure 4:
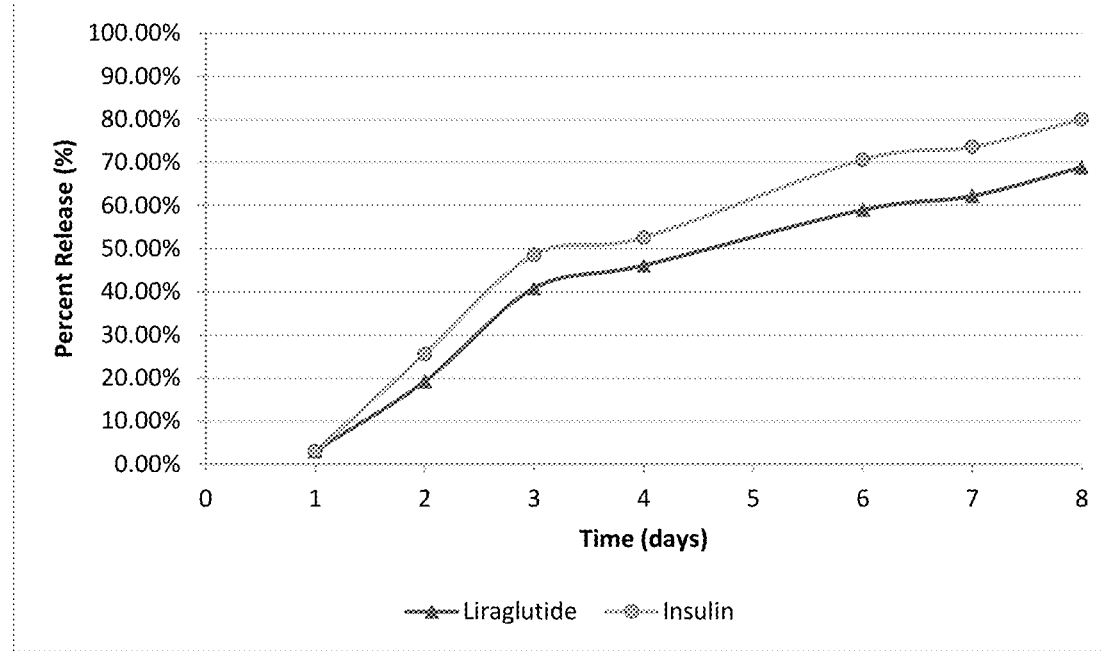
FIG. 4 shows cumulative % release for liraglutide and rh-insulin from liraglutide/rh-insulin-A9.

The in vitro dissolution profile for both liraglutide and Insulin from insulin/liraglutide-A9 is plotted in FIG. 4.

Example 6. Preparation and In Vitro Analysis of Ropivacaine Metabolite with A9

10 mg of Ropivacaine metabolite were placed in a 20 mL sintered glass vial. A9 was added with 1:0.5 weight ratio or 1:1 weight ratio of Ropivacaine metabolite to A9, with 100 uL of dimethyl sulfoxide and the mixture was stirred at 100 rpm for 5 min at 37° C. (until it became a visibly clear solution), to provide Ropivacaine metabolite-A9.

Ropivacaine Metabolite in Diluent (Control):

10 mg of ropivacaine metabolite was placed in a 20 mL sintered glass vial and 100 uL of dimethyl Sulfoxide or dimethyl Formamide and the mixture was stirred at 100 rpm for 5 min at 37° C. (until it became a visibly clear solution).

For dissolution or in vitro release testing, PBS (Phosphate buffered saline) pH of about 7.4 was used as the medium, and the solutions of ropivacaine metabolite was dispersed into the dissolution medium. For the dissolution study, a known amount of Ropivacaine metabolite (20 uL of above solution contains 2 mg of ropivacaine metabolite) was placed into 2 mL conical shaped polypropylene vials. 1 mL release medium (0.01M PBS at pH 7.4 equilibrated at 37° C.) was added gently to each vial such that the surface of the formulation was not disturbed. The samples were placed at 37° C./100 rpm in an orbital shaker. At every time point essentially for all the release medium was removed and replaced by fresh solution. The amount of ropivacaine metabolite in solution at each time point was determined by HPLC.

Results

Figure 5:
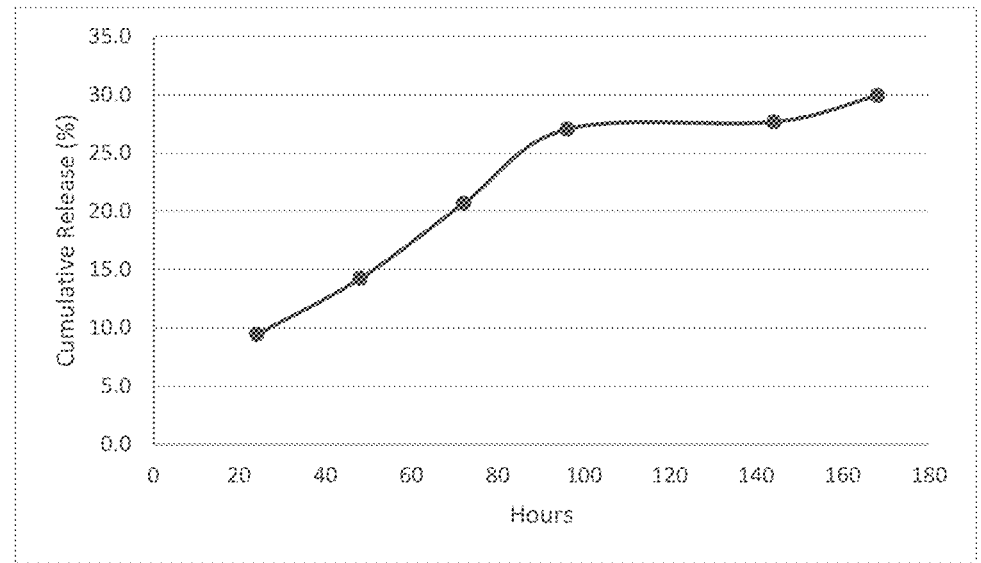
FIG. 5 shows cumulative % release for ropivacaine metabolite from ropivacaine metabolite-A9.
Figure 6:
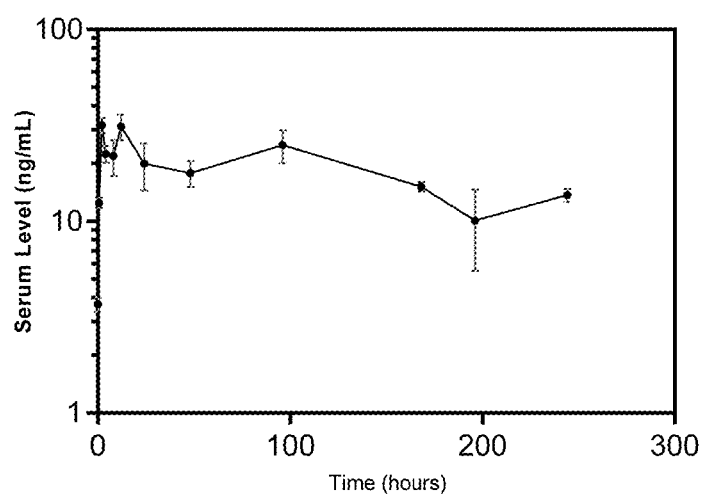
FIG. 6 shows results of in vivo serum level for liraglutide from liraglutide-A6.
Figure 7:
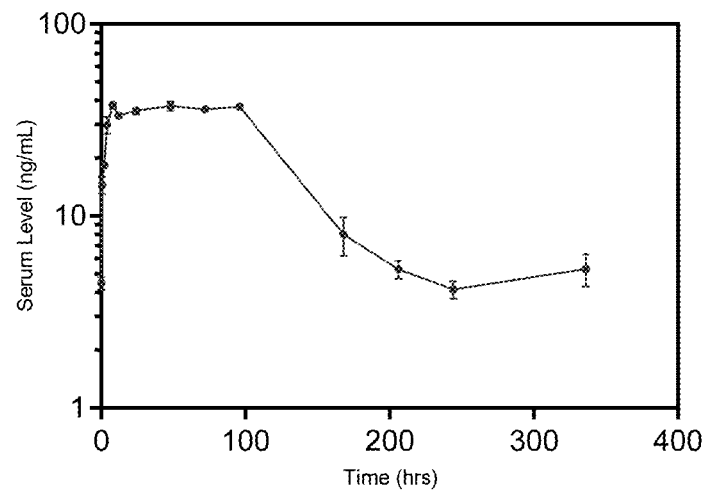
FIG. 7 shows results of in vivo serum level for liraglutide from liraglutide-A9.
Figure 8:
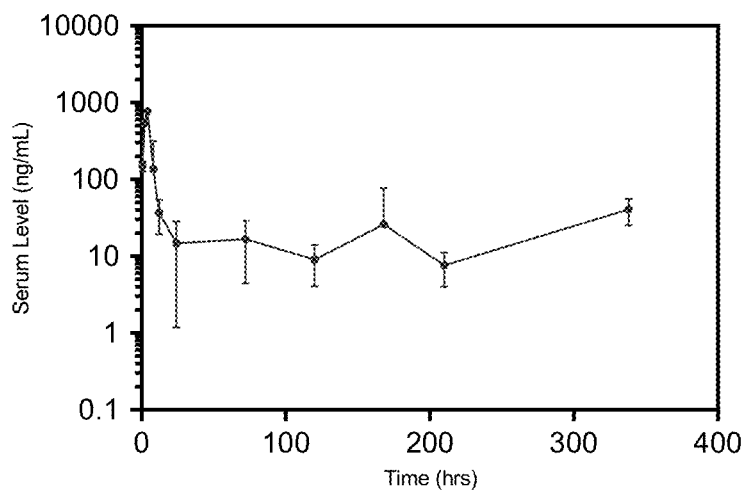
FIG. 8 shows results of in vivo serum level for insulin glargine from insulin glargine-A6.
Figure 9:
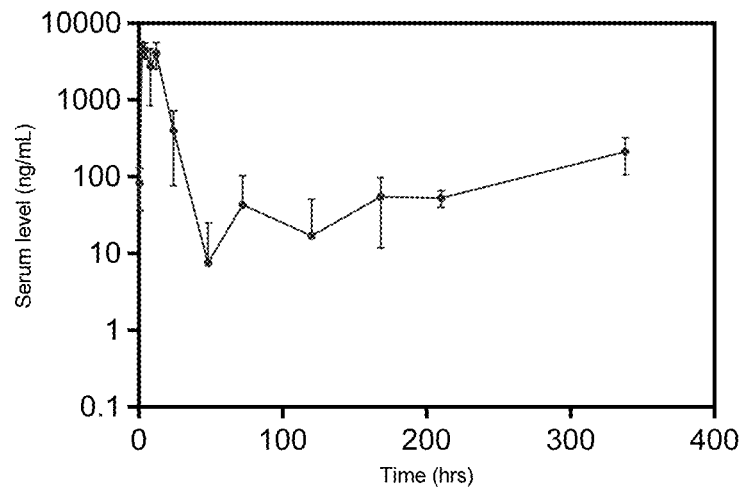
FIG. 9 shows results of in vivo serum level for rh-insulin from rh-insulin-A9.
Figure 10:
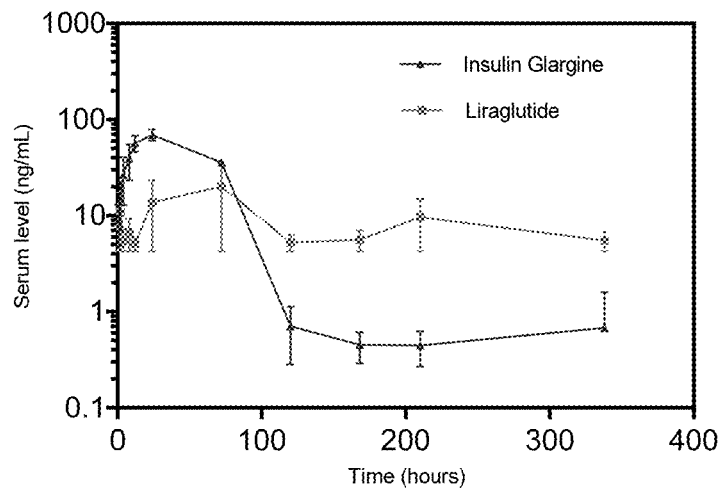
FIG. 10 shows results of in vivo serum level for liraglutide and insulin glargine from liraglutide-insulin glargine-A9.
Figure 11:
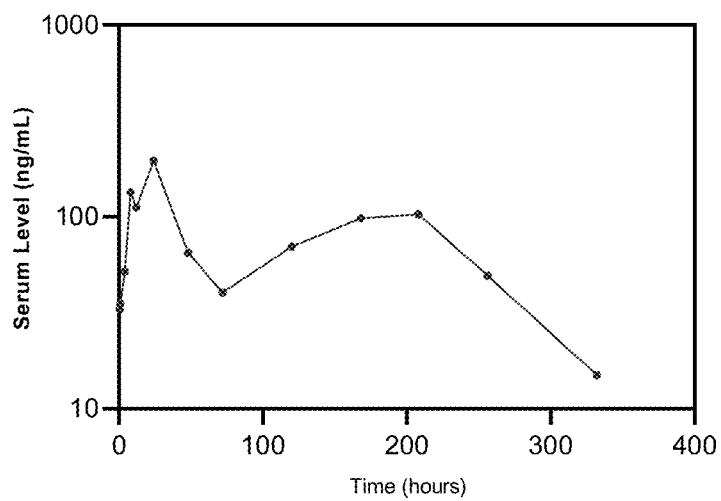
FIG. 11 shows results of in vivo serum level for liraglutide from liraglutide-A9.
Figure 12:
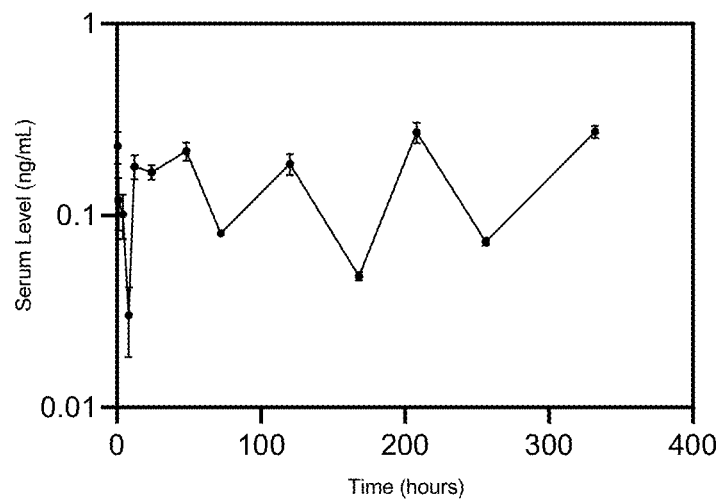
FIG. 12 shows results of in vivo serum level for rh-insulin from rh-insulin-A9.
Figure 13:
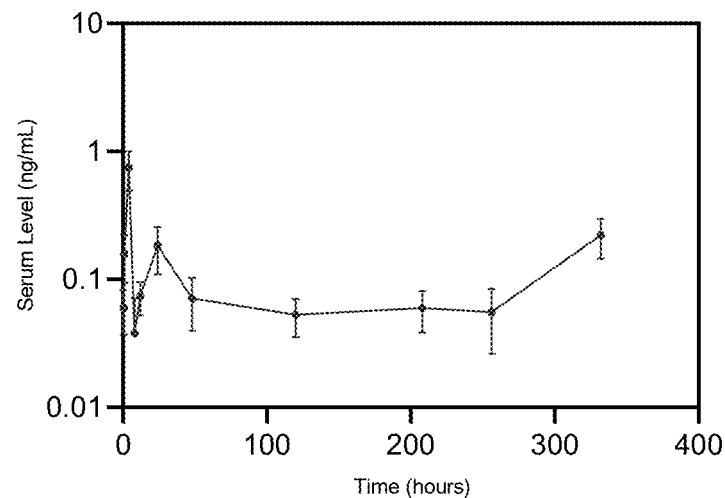
FIG. 13 shows results of in vivo serum level for insulin glargine from insulin glargine-A9.
Figure 14:
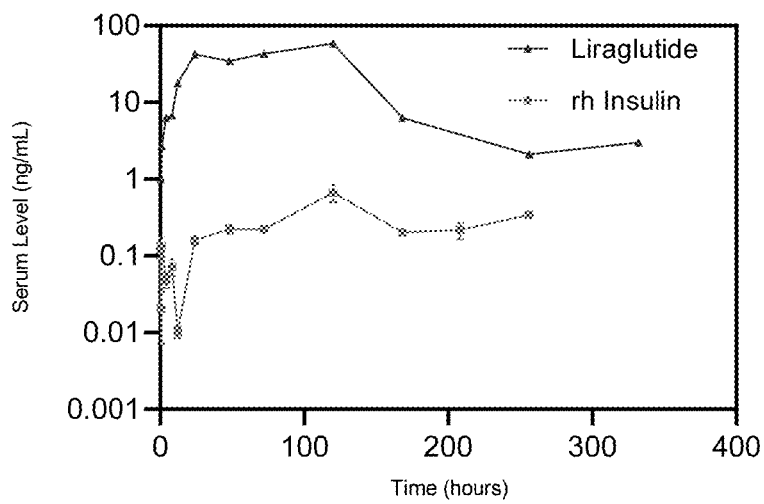
FIG. 14 shows results of in vivo serum level for liraglutide and rh-insulin from liraglutide-rh-insulin-A9.

The in vitro dissolution profile showing cumulative release (%) for Ropivacaine metabolite from ropivacaine metabolite-A9 is plotted in FIG. 5.

Example 7: Preparation and In Vivo Analysis of Liraglutide, Rh-Insulin and Insulin Glargine with A6 or A9

The compositions of each of liraglutide, rh-Insulin and Insulin glargine with A6 or A9 were prepared by methods similar to those described above and were used in the in vivo study in rats. Specifically, six different groups were subjected to the different compositions listed in Table 1. The compositions were injected to the rats. The pharmacokinetic profiles for groups 1-5 are provided in FIGS. 6-10 respectively. Dosing rates (mg/kg) varied across the test groups and among animals within a given test group.

TABLE 1

| Group # | Liraglutide | Insulin | Peptide |
|---|---|---|---|
| Group 1 | 2 mg | — | A6, 10 mg |
| Group 2 | 2 mg | — | A9, 10 mg |
| Group 3 | — | insulin glargine, 2 mg | A6, 10 mg |
| Group 4 | — | rh-insulin, 2 mg | A9, 10 mg |
| Group 5 | 2 mg | insulin glargine, 2mg | A9, 20 mg |

Another in vivo study was done in rats with the compositions of each of liraglutide, rh-insulin and insulin glargine with A9. Specifically, four different groups were subjected to the different compositions listed in Table 2. FIGS. 11-14 provide the geometric mean data for the serum levels of the pharmaceutically active compounds (liraglutide, rh-insulin or insulin glargine) in this study.

TABLE 2

| Group # | Liraglutide | Insulin (mg) | Peptide (mg) |
|---|---|---|---|
| Group 1 | 2 mg | — | A9, 20 mg |
| Group 2 | — | rh-insulin, 2 mg | A9, 20 mg |
| Group 3 | — | insulin glargine, 2 mg | A9, 20 mg |
| Group 4 | 2 mg | rh-insulin, 2 mg | A9, 40 mg |

Example 8: Local Tolerability Following Injection in Rats

Histopathological assessment of skins from the rats injected in Example 7 was performed using standard procedures. In general, there was minimal to mild inflammation present in the deep dermis in all groups at both the vehicle and active sites. This indicates that there is some nonspecific local multifocal inflammation induced by all of the peptides of formula I tested herein and diluent and the test article. There were also low numbers of small granulomas present in the deep dermis in a few animals in most groups in both the control and active groups. These are considered to be a resolving foreign body reaction or granuloma formulation reaction to the test and vehicle articles. This indicates that both the test article and the various vehicles alone or with test article will induce a small local foreign body reaction or granuloma formation particularly in Table 2 Groups 2, 3, and 4, where the pharmaceutically active molecule is insulin.

Example 9. Preparation and In Vitro Analysis of Ketamine with A7

Figure 15:
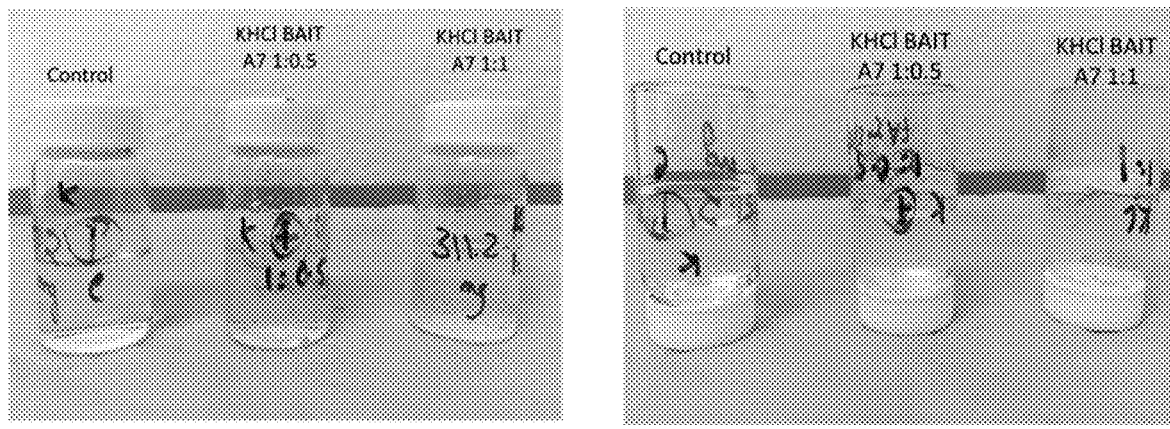
FIG. 15 shows vials containing Ketamine HCl aqueous bolus compared to Ketamine HCl-A7 formulations indicating gel formation due to Ketamine-A7.

500 mg of ketamine were placed in a 20 mL sintered glass vial. As seen in FIG. 15, different ratio of Ketamine HCL and A7 were added, with 1:0.5 weight ratio or 1:1 weight ratio of Ketamine HCL-A7, with 500 uL of dimethyl sulfoxide and the mixture was stirred at 100 rpm for 5 min at 37° C. (until it became a visibly suspension solution) to provide Ketamine HCL-A7.

Ketamine in Diluent (Control)

500 mg of Ketamine was placed in a 20 mL sintered glass vial and 500 uL of dimethyl sulfoxide or dimethyl formamide were added and the mixture was stirred at 100 rpm for 5 min at 37° C. (until it became a visibly suspension solution).

In Vitro Analysis of Ketamine Release

Dissolution experiments were conducted as set forth below to determine the in vitro release of Ketamine from Ketamine-A7 prepared above.

For dissolution or in vitro release testing, PBS (phosphate buffered saline) pH of about 7.4 was used as the medium, and the solutions of liraglutide was dispersed into the dissolution medium. For the dissolution study, a known amount of Ketamine (100 uL of above solution contains 100 mg of Ketamine) was placed into 2 mL conical shaped polypropylene vials. 1 mL release medium (0.01M PBS at pH 7.4 equilibrated at 37° C.) was added gently to each vial such that the surface of the formulation was not disturbed. The samples were placed at 37° C./100 rpm in an orbital shaker. At every time point essentially all the release medium was removed and replaced by fresh solution. The amount of ketamine in solution at each time point was determined by HPLC.

Results

Figure 16:
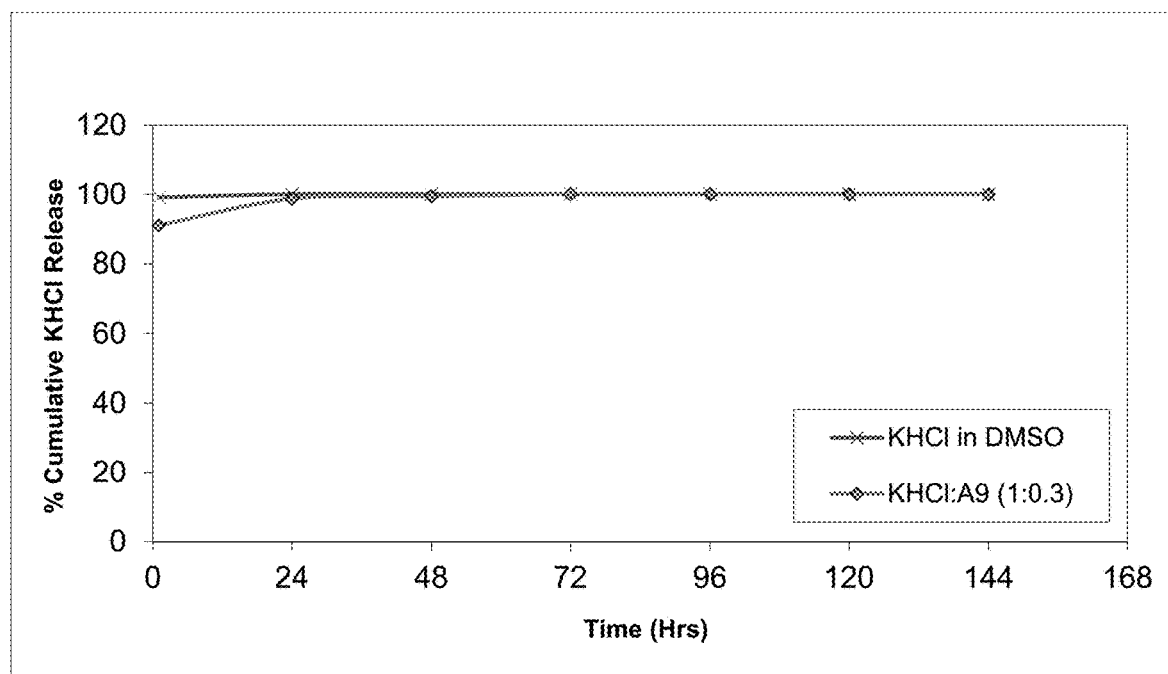
FIG. 16 shows cumulative % release for Ketamine HCl from Ketamine HCl-A9.
Figure 17:
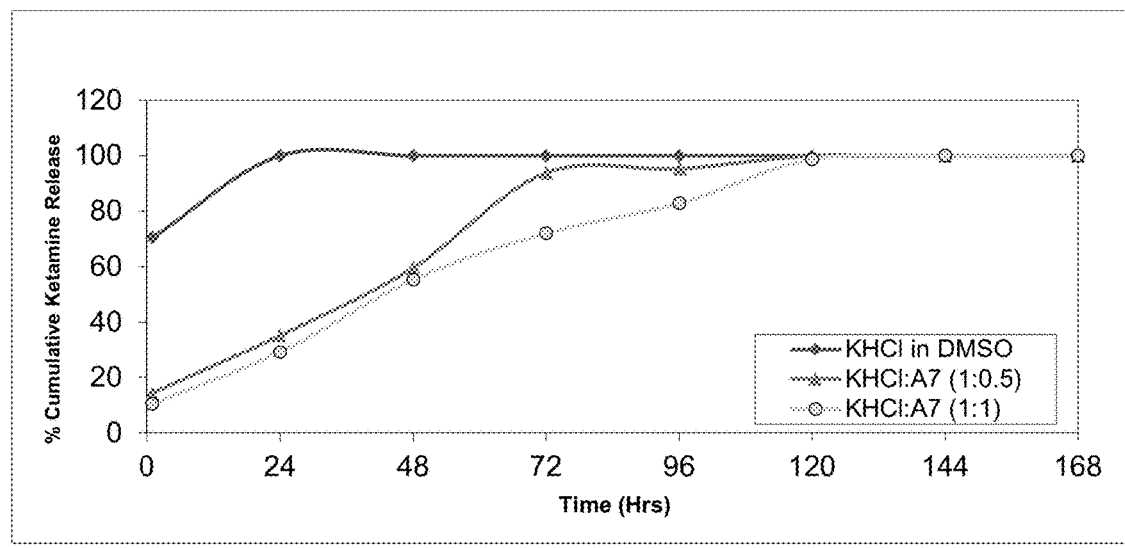
FIG. 17 shows cumulative % release for Ketamine HCl from Ketamine HCl-A7.
Figure 18:
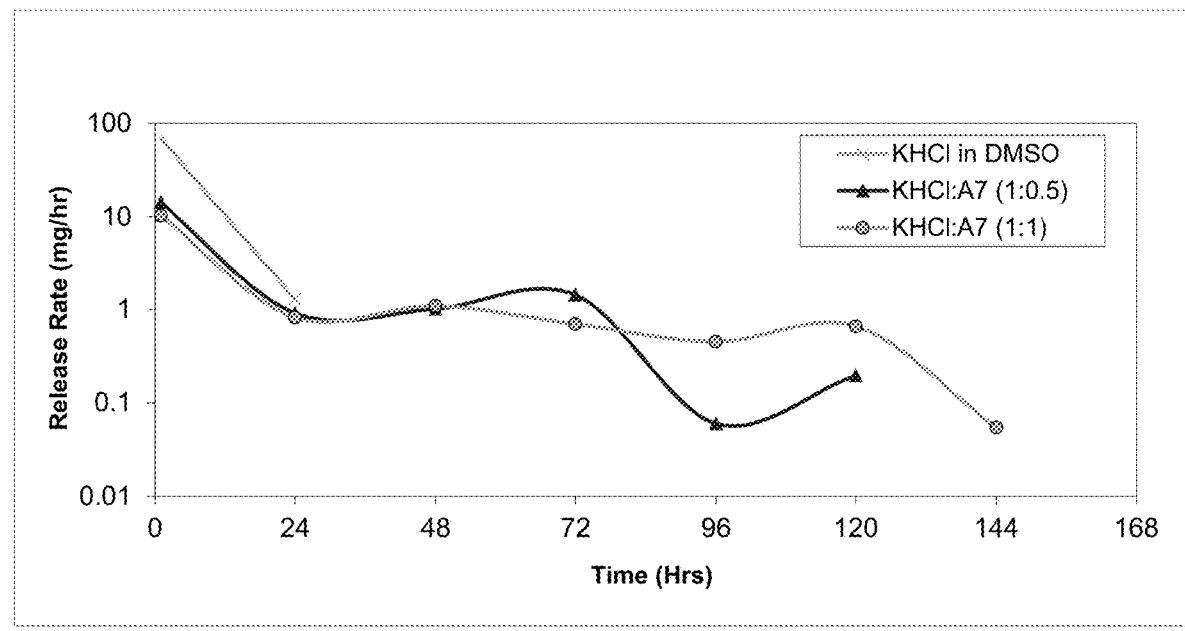
FIG. 18 shows Release rate for Ketamine HCl from Ketamine HCl-A7 at two different ratios (1:0.5 and 1:1).

The in vitro dissolution profile for Ketamine HCL from Ketamine HCL-A9 (with a 1:0.3 weight ratio) is plotted in FIG. 16. The in vitro dissolution profile for Ketamine HCL from Ketamine HCL-A7 (with a 1:0.5 weight ratio and with 1:1 weight ration) is plotted in FIG. 17 and FIG. 18. The in vitro release of Ketamine HCL showed more controlled release when Ketamine HCL to A7 ratio is 1:1.

Example 10. Preparation and In Vitro Analysis of Etanercept with A9

50 mg of Etanercept were placed in a 20 mL sintered glass vial. Different ratio of liraglutide and A7 were added, with 1:0.5 weight ratio or 1:1 weight ratio of Etanercept A9, with 500 uL of dimethyl sulfoxide and the mixture was stirred at 100 rpm for 5 min at 37° C. (until it became a visibly suspension solution) to provide Etanercept-A9.

Etanercept in Diluent (Control)

50 mg of Etanercept was placed in a 20 mL sintered glass vial and 500 uL of dimethyl sulfoxide or dimethyl formamide were added and the mixture was stirred at 100 rpm for 5 min at 37° C. (until it became a visibly suspension solution).

In Vitro Analysis of Etanercept Release

Figure 19:
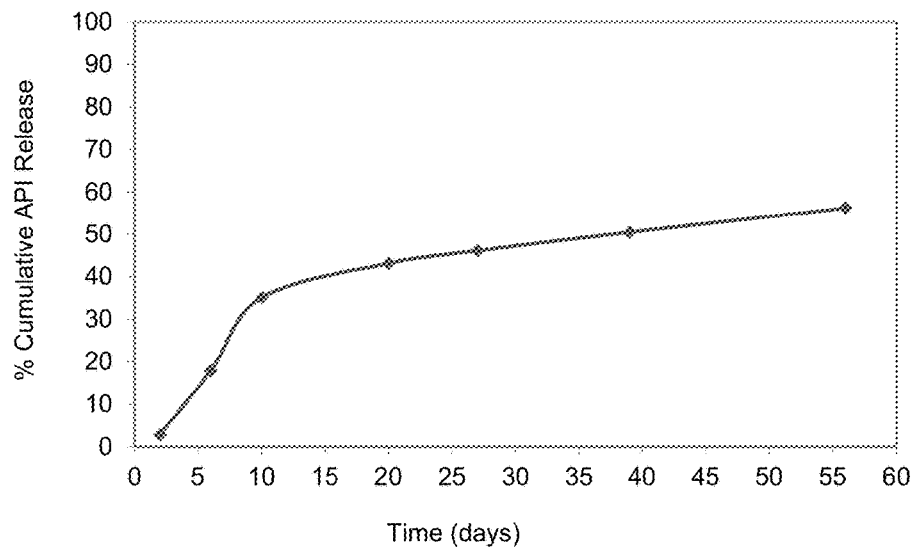
FIG. 19 shows % cumulative release for Etanercept from Etanercept-A9.

Dissolution experiments were conducted as set forth below to determine the in vitro release of Etanercept from Etanercept-A9 prepared above. The in vitro dissolution profile for Etanercept from Etanercept-A9 is plotted in FIG. 19.

For dissolution or in vitro release testing, PBS (phosphate buffered saline) pH of about 7.4 was used as the medium, and the solutions of liraglutide was dispersed into the dissolution medium. For the dissolution study, a known amount of Etanercept (100 uL of above solution contains 100 mg of Etanercept) was placed into 2 mL conical shaped polypropylene vials. 1 mL release medium (0.01M PBS at pH 7.4 equilibrated at 37° C.) was added gently to each vial such that the surface of the formulation was not disturbed. The samples were placed at 37° C./100 rpm in an orbital shaker. At every time point essentially all the release medium was removed and replaced by fresh solution. The amount of Etanercept in solution at each time point was determined by HPLC.

The present disclosure is not to be limited in scope by the specific embodiments described which are intended as single illustrations of individual aspects of the disclosure, and any compositions or methods which are functionally equivalent are within the scope of the disclosure. It will be apparent to those skilled in the art that various modifications and variations can be made in the methods and compositions of the present disclosure without departing from the spirit or scope of the disclosure. Thus, it is intended that the present disclosure cover the modifications and variations of the disclosure provided they come within the scope of the appended claims and their equivalents.

All publications and patent applications mentioned in this specification are herein incorporated by reference to the same extent as if each individual publication or patent application was specifically and individually indicated to be incorporated by reference.

The invention claimed is:

1. A composition comprising:
   i) a pharmaceutically active compound having a log P value of less than 4; and
   ii) a peptide of formula I':

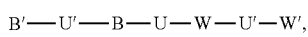

$$B'—U'—B—U—W—U'—W',\quad I'$$

wherein:
   each of B, B', W and W' independently is a peptide comprising at least 75% acidic amino acids or 75% basic amino acids, provided that when B is a peptide having at least 75% acidic amino acids, W is a peptide having at least 75% basic amino acids or vice versa;
   each of U and U' independently is a peptide comprising neutral amino acids;
   each of B, U and W independently comprises 2 to 9 amino acids; and
   each of B', U' and W' independently comprises 2 to 9 amino acids or the adjacent U' and W' are absent or the adjacent B' and U' are absent or all B', U' and W' are absent; provided that the peptide of formula I' comprises from about 9 to 21 amino acids.

2. The composition of claim 1, wherein the acidic amino acids are independently selected from aspartic acid or glutamic acid.

3. The composition of claim 1, wherein the basic amino acids are independently selected from lysine, arginine or histidine.

4. The composition of claim 1, wherein the neutral amino acids are independently selected from tryptophan, phenylalanine, glycine, alanine, valine, isoleucine, leucine, serine, threonine, tyrosine, asparagine, glutamine, and proline.

5. The composition of claim 1, wherein B comprises 100% acidic amino acids and W comprises 100% basic amino acids or vice versa.

6. The composition of claim 1, wherein each of B, U and W comprises 3 amino acids.

7. The composition of claim 1, wherein the peptide of formula I' comprises the amino acid sequence of RRRRRRLLLAAAEEE (SEQ ID NO:2), KKKKKKLLLAAAEEE (SEQ ID NO:3), RRRRRLLLAAAEE (SEQ ID NO:4), RRRLLLEEE (SEQ ID NO:5), RRRRRLLLEEEEE (SEQ ID NO:6), RRRRRLLLLLEEEEE (SEQ ID NO:1), RRRRRRRLLLLLLLEEEEEEE (SEQ ID NO: 16), EEEEELLLLLRRRRR (SEQ ID NO: 7), RRRLLLEEELLLRRR (SEQ ID NO: 14), or RRRRRLLLLLDDDDD (SEQ ID NO: 8).

8. The composition of claim 1, wherein the pharmaceutically active compound is an analgesic agent, an anesthetic agent, an anti-asthmatic agent, an antibiotic, an anti-depressant agent, an anti-diabetic agent, an anti-fungal agent, an anti-hypertensive agent, an anti-inflammatory agent, an anti-neoplastic agent, an anxiolytic agent, an immunostimulating agent or an immunosuppressive agent.

9. The composition of claim 1, wherein the pharmaceutically active compound is a small molecule.

10. The composition of claim 1, wherein the pharmaceutically active compound is a large molecule selected from antibody, peptide, nanobody, antibody fragments, FAB fragment, affibody, protein, nucleotide and trinectin derivatives.

11. The composition of claim 10, wherein the large molecule is a protein or a nucleotide.

12. The composition of claim 1, wherein the weight ratio of the pharmaceutically active compound to the peptide of formula I' is from about 1:0.5 to about 1:12.

13. The composition of claim 7, wherein the peptide of formula I' comprises the amino acid sequence of RRRRRLLLLLEEEEE (SEQ ID NO:1).

14. A controlled release formulation comprising:
i) a pharmaceutically active compound having a log P value of less than 4; and
ii) a peptide of formula I':

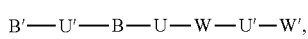

wherein:
each of B, B', W and W' independently is a peptide comprising at least 75% acidic amino acids or 75% basic amino acids, provided that when B is a peptide having at least 75% acidic amino acids, W is a peptide having at least 75% basic amino acids or vice versa;
each of U and U' independently is a peptide comprising neutral amino acids;
each of B, U and W independently comprises 2 to 9 amino acids; and
each of B', U' and W' independently comprises 2 to 9 amino acids or the adjacent U' and W' are absent or the adjacent B' and U' are absent or all B', U' and W' are absent; provided that the peptide of formula I' comprises from about 9 to 21 amino acids,
wherein release of the pharmaceutically active compound is controlled by adjusting weight ratio of the pharmaceutically active compound to the peptide of formula I'.

15. A peptide of formula I':
wherein:

each of B, B', W and W' independently is a peptide comprising at least 75% acidic amino acids or 75% basic amino acids, provided that when B is a peptide having at least 75% acidic amino acids, W is a peptide having at least 75% basic amino acids or vice versa;
each of U and U' independently is a peptide comprising neutral amino acids;
each of B, U and W independently comprises 2 to 9 amino acids; and
each of B', U' and W' independently comprises 2 to 9 amino acids or the adjacent U' and W' are absent or the adjacent B' and U' are absent or all B', U' and W' are absent; provided that the peptide of formula I' comprises from about 9 to 21 amino acids.

16. The peptide of claim 15, wherein the peptide of formula I' comprises the amino acid sequence of RRRRRRLLLAAAEEE (SEQ ID NO:2), KKKKKKLLLAAAEEE (SEQ ID NO:3), RRRRRLLLAAAEE (SEQ ID NO:4), RRRLLLEEE (SEQ ID NO:5), RRRRRLLLEEEEE (SEQ ID NO:6), RRRRRLLLLLEEEEE (SEQ ID NO:1), RRRRRRRLLLLLLLEEEEEEE (SEQ ID NO:16), EEEEELLLLLRRRRR (SEQ ID NO:7), RRRLLLEEELLLRRR (SEQ ID NO:14), or RRRRRLLLLLDDDDD (SEQ ID NO:8).

17. A drug delivery method comprising administering to a subject in need thereof a composition comprising:
i) a pharmaceutically active compound having a log P value of less than 4; and
ii) a peptide of formula I':

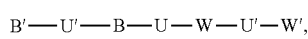

wherein:
each of B, B', W and W' independently is a peptide comprising at least 75% acidic amino acids or 75% basic amino acids, provided that when B is a peptide having at least 75% acidic amino acids, W is a peptide having at least 75% basic amino acids or vice versa;
each of U and U' independently is a peptide comprising neutral amino acids;
each of B, U and W independently comprises 2 to 9 amino acids; and
each of B', U' and W' independently comprises 2 to 9 amino acids or the adjacent U' and W' are absent or the adjacent B' and U' are absent or all B', U' and W' are absent; provided that the peptide of formula I' comprises from about 9 to 21 amino acids.

* * * * *